(12) United States Patent
Rovira et al.

(10) Patent No.: US 7,064,828 B1
(45) Date of Patent: Jun. 20, 2006

(54) PULSED SPECTROSCOPY WITH SPATIALLY VARIABLE POLARIZATION MODULATION ELEMENT

(75) Inventors: Pablo I. Rovira, San Francisco, CA (US); Lars Markwort, Saratoga, CA (US)

(73) Assignee: Nanometrics Incorporated, Milpitas, CA (US)

( * ) Notice: Subject to any disclaimer, the term of this patent is extended or adjusted under 35 U.S.C. 154(b) by 439 days.

(21) Appl. No.: 10/027,940

(22) Filed: Dec. 19, 2001

(51) Int. Cl.
*G01J 4/00* (2006.01)

(52) U.S. Cl. ....................................... 356/369
(58) Field of Classification Search ........ 356/364–369; 250/225
See application file for complete search history.

(56) References Cited

U.S. PATENT DOCUMENTS

| | | | | |
|---|---|---|---|---|
| 4,105,338 A | * | 8/1978 | Kuroha ........................ | 356/365 |
| 4,298,283 A | | 11/1981 | Makosch et al. ............ | 356/495 |
| 4,508,832 A | * | 4/1985 | Carter et al. ................. | 436/517 |
| 4,583,855 A | | 4/1986 | Baraket ....................... | 356/491 |
| 4,859,017 A | | 8/1989 | Brierley et al. .............. | 385/27 |
| 4,872,755 A | | 10/1989 | Kuchel ........................ | 356/495 |
| 4,931,657 A | * | 6/1990 | Houston et al. .......... | 250/559.08 |
| 5,076,696 A | * | 12/1991 | Cohn et al. .................. | 356/369 |
| 5,373,359 A | * | 12/1994 | Woollam et al. ............ | 356/328 |
| 5,502,567 A | | 3/1996 | Pokrowsky et al. ........ | 356/367 |
| 5,561,525 A | | 10/1996 | Toyonaga et al. ........... | 356/512 |
| 5,754,296 A | * | 5/1998 | Law .............................. | 356/369 |
| 5,889,593 A | | 3/1999 | Bareket ....................... | 356/445 |
| 6,002,477 A | | 12/1999 | Hammer ..................... | 356/307 |
| 6,052,188 A | * | 4/2000 | Fluckiger et al. ........... | 356/369 |
| 6,122,052 A | | 9/2000 | Barnes et al. ................ | 356/328 |
| 6,134,012 A | * | 10/2000 | Aspnes et al. ............... | 356/369 |
| 6,160,621 A | | 12/2000 | Perry et al. .................. | 356/381 |
| 6,201,609 B1 | | 3/2001 | Hill et al. .................... | 356/491 |
| 6,275,291 B1 | | 8/2001 | Abraham et al. ........... | 356/367 |
| 6,304,330 B1 | | 10/2001 | Millerd et al. .............. | 356/521 |
| 6,392,116 B1 | | 5/2002 | Beihoffer et al. ........... | 356/351 |

(Continued)

FOREIGN PATENT DOCUMENTS

| | | |
|---|---|---|
| EP | 0 987 537 A2 | 3/2000 |
| WO | WO 02/15238 A2 | 2/2002 |
| WO | WO 02/16893 A2 | 2/2002 |

OTHER PUBLICATIONS

Azzram, R., "An arrangement of two reflective photodetectors for measuring all four Stokes parameters of light", *American Institute of Physics* (1991) pp. 2080-2082.

(Continued)

*Primary Examiner*—Hoa Q. Pham
(74) *Attorney, Agent, or Firm*—Silicon Valley Patent Group LLP (57) ABSTRACT

A metrology device, such as an ellipsometer, includes a light source that produces a pulsed electromagnetic beam, such as a flash bulb or pulsed laser, and a spatially dependent polarizing element that introduces a spatially dependent retardation in the light beam. The use of a pulsed light source is advantageous over a continuous light source, as a pulsed light source generates less heat, is stronger, lasts longer, and does not need the use of a mechanical shutter. The use of a spatially dependent polarizing element advantageously eliminates the use of temporally dependent moving polarization modulation elements, thereby allowing the use of a pulsed light source. Downstream of the spatially dependent polarizing element are the analyzer and a multi-element detector that may be synchronized with the pulsed electromagnetic beam to detect after one or several pulses of light have been emitted from the pulsed light source.

16 Claims, 8 Drawing Sheets

U.S. PATENT DOCUMENTS

| | | | |
|---|---|---|---|
| 6,452,682 B1 | 9/2002 | Hill et al. | 356/493 |
| 6,515,745 B1 | 2/2003 | Vurens et al. | 356/369 |
| 6,525,829 B1* | 2/2003 | Powell et al. | 356/630 |
| 6,583,875 B1* | 6/2003 | Wei et al. | 356/369 |
| 2003/0020912 A1 | 1/2003 | Norton et al. | 356/369 |
| 2005/0036143 A1* | 2/2005 | Huang | 356/369 |

OTHER PUBLICATIONS

Bennett, J., "Polarizers" *Optical Elements*, Chapter 3, pp. 3.1-3.70.

Cumming, D. et al., "A variable polarisation compensator using artificial dielectrics" Elsevier Science (1999) pp. 164-168.

Hauge, P., "Recent Developments In Instrumentation In Ellipsometry", *Surface Science* 96 (1980) pp. 108-140.

Horn, T., "Liquid Crystal Imaging Stokes Polarimeter", *Astronomical Society of the Pacific* (1999) pp. 33-37.

Jasperson, S., "A Modulated Ellipsometer For Studying Thin Film Optical Properties And Surface Dynamics" *Surface Science* 37 (1973) pp. 548-558.

Kazama, A. et al., "Compact and high-speed ellipsometer" *SPIE* vol. 1681 pp. (1992) 183-188.

Lee, J. et al., "Rotating-compensator multichannel ellipsometry: Applications for real time Stokes vector spectroscopy of thin film growth", *Review of Scientific Instruments* 69 (1998) pp. 1800-1810.

Oliva, E., "Wedged double Wollaston, a device for single shot polarimetric measurements", *Astronomy & Astrophysics Supplement Series* 123 (1977) pp. 589-592.

Smajkiewicz, A., "An Argument for a Filter Array vs. Linear Variable Filter in Precision Analytical Instrument Applications".

"Stokes Polarimetry Using Liquid-Crystal Variable Retarders", downloaded Jun. 11, 2001 from <http://www.meadowlark.com/AppNotes/appnote3.htm>, Meadowlark Optics, Inc. (1998-2001).

Chapter 3, Ellipsometer Systems, "Theory and Analysis of Measurements in Ellipsometer Systems" pp. 167-268.

Azzam, R.M.A. et al., *Ellipsometry and Polarized Light*, Chapter 3, "Theory and Analysis of Measurements in Ellipsometer Systems" (1987) pp. 167-268.

\* cited by examiner

Fig. 1
(Conventional)

Fig. 2
(Conventional)

PULSED SPECTROSCOPY WITH SPATIALLY VARIABLE POLARIZATION MODULATION ELEMENT

FIELD OF THE INVENTION

The present invention is related to optical metrology and in particular to a metrology device and technique that uses a pulsed light source and a spatially dependent polarizing element as a component of an ellipsometer or a polarized spectrometer.

BACKGROUND

There is always a need for precise and reliable metrology to monitor the properties of thin films, especially in the semiconductor and magnetic head industries. Thin film properties of interest include the thickness of one or more layers, the surface roughness, the interface roughness between different layers, the optical properties of the different layers, the compositional properties of the different layers and the compositional uniformity of the film stack. Ellipsometry is particularly well suited to this task when the thickness is less than 100 nm, when there are more than two layers present or when there are compositional variations. Additionally, dimensional measurements such as linewidth, sidewall angle, and height can be extracted using ellipsometry and/or reflectometry.

Figure 1:
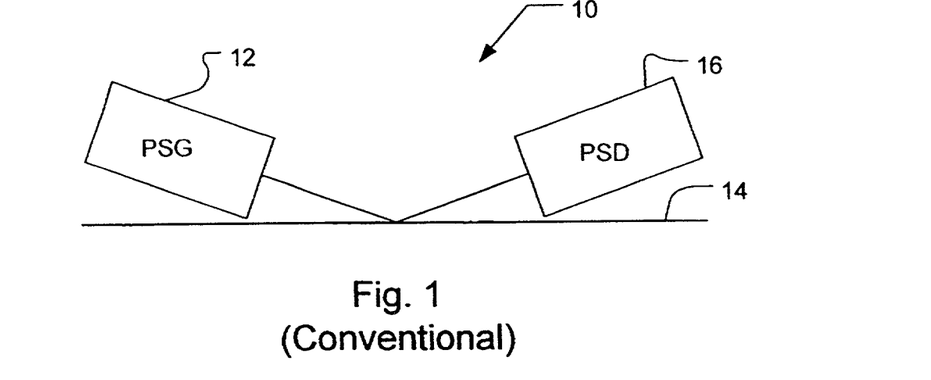
FIG. 1 shows a simple block diagram view of a typical ellipsometer including a Polarization State Generator (PSG), a sample and a Polarization State Detector (PSD).

An ellipsometer is a measurement tool used to determine the change in polarization state of an electromagnetic wave after interaction with a sample. The determination of this polarization state can yield information about the thin film properties such as those listed above. In general, an ellipsometer is a polarization-state-in, polarization-state-out device. FIG. 1 shows a simple block diagram of a typical ellipsometer 10, which includes a Polarization State Generator (PSG) 12 that generates an electromagnetic wave of a known polarization state and a Polarization State Detector (PSD) 16 that determines the polarization state of the electromagnetic wave after interaction with a sample 14. In FIG. 1 the interaction is shown in reflection mode, but it should be understood that the interaction may be in transmission mode, i.e., the PSD determines the polarization state of the electromagnetic wave after transmission through a sample. Different kinds of PSG/PSD configurations have been proposed and developed for ellipsometers. The advantages of each configuration are specific to the kind of extracted information that is desired.

The use of pulsed light source in metrology devices offers many advantages over conventional continuous light sources, as discussed in U.S. Pat. No. 6,002,477 to Hammer. A pulsed light source enables energization of the light source to be confined to the time over which a measurement is to be made, thereby reducing power consumption and very significantly extending the life of the light source.

In the thin film metrology field, the most popular ellipsometry configurations include a rotating polarizing element in the PSG and/or the PSD. Unfortunately, rotating polarizing elements cannot be used with pulsed light sources such as flash bulbs or pulsed lasers. When a rotating polarizing element is used with a pulsed light source, synchronization problems occur, resulting in inaccurate information being extracted. Furthermore, the light source intensity must be very constant over a whole optical rotation when using rotating elements, which is not possible with a pulsed light source, where the light source intensity varies significantly from pulse to pulse. This problem is aggravated for spectroscopic ellipsometry, where usually a multi-channel detector is utilized to record the whole spectrum. Such a photodiode array generally has a minimum reading time, which makes the use of a pulsed source in conjunction with a rotating element impossible.

Figure 2:
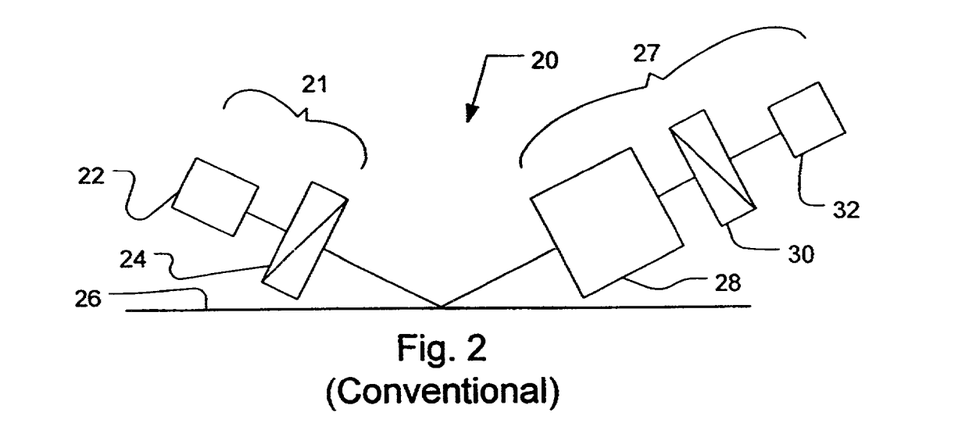
FIG. 2 is a block diagram of a conventional photoelastic modulator ellipsometer (PME).

A different kind of ellipsometer that has been extensively developed and used for thin film metrology and that does not have a rotating element is the photoelastic modulator ellipsometer (PME). This instrument employs a photoelastic modulator (PM) to change the polarization state of the light as a function of time either before or after reflection from the sample surface. FIG. 2 is a block diagram of a conventional PME 20. The PSG portion 21 of the PME 20 includes a light source 22 and a linear polarizer 24. The light source 22 generates a collimated beam (monochromatic or broadband radiation) that is transmitted through the linear polarizer 24. The linearly polarized beam is reflected from the sample surface 26 thereby modifying the polarization state of the electromagnetic beam. The PSD portion 27 of the PME 20 includes a PM (or Pockels cell) 28, another linear polarizer 30, and a detector 32.

Unfortunately, photoelastic modulators and Pockels cells introduce a time dependent phase that creates synchronization problems when used with a pulsed light source, similar to those seen in ellipsometers utilizing a rotating polarizing element. Thus, a pulsed light source is impractical in conjunction with an ellipsometer configuration that utilizes a photoelastic modulator or Pockels cell.

What is needed is an ellipsometer configuration (monochromatic or spectroscopic) that does not use moving parts or a phase modulator, i.e., a configuration that is time-independent so that it can be used with a pulsed light source, with the advantage over a continuous light source being that a pulsed light source generates less heat, is more intense and has a longer lifetime. Moreover, such an ellipsometer can be compact and robust, minimizing cost and maintenance. Such a configuration will be particularly suitable for integration into existing process tools due to its reduced size.

SUMMARY

A metrology device, such as an ellipsometer, in accordance with one embodiment of the present invention, includes a variable retarder that introduces a spatially dependent phase shift to an electromagnetic beam. A polarizer and multi-element detector then spatially sample the phase-shifted beam. This is in contrast to the analysis of a time dependent phase shifted beam used in conventional systems. A metrology device, in accordance with one embodiment of the present invention, advantageously, has no moving parts, is compact and utilizes inexpensive components.

Accordingly, in one aspect of the present invention, a metrology device that detects the polarization state of a pulsed electromagnetic beam that is incident on a sample includes a polarization state generator with an electromagnetic source that turns on and off to produce a pulsed electromagnetic beam, wherein the polarization state generator produces a pulsed electromagnetic beam of known polarization state that is incident on the sample. The metrology device includes a spatially dependent polarizing element in the path of the expanded electromagnetic beam and a multi-element detector within the path of the pulsed electromagnetic beam after the spatially dependent polarizing element, wherein the multi-element detector measures the intensity of the pulsed electromagnetic beam as a function of position. The metrology device may include a beam expander that spatially expands the electromagnetic beam to a desired size. The metrology device may operate in a spectroscopic mode, in which case the device includes a monochromator or spectrograph. The metrology device may include a synchronizer coupled to the electromagnetic source and the multi-element detector, wherein the synchronizer causes the multi-element detector to measure the intensity of the pulsed electromagnetic beam as a function of position and is time correlated to read out data when the pulsed electromagnetic source is off, i.e., not producing light. The electromagnetic source may also produce a plurality of pulsed electromagnetic beams after the synchronizer causes the multi-element detector to stop reading out the data, i.e., the collected signal can be averaged over multiple consecutive light pulses.

Another aspect of the present invention includes a method of ellipsometrically measuring a sample. The method includes turning on and off an electromagnetic beam to produce a pulsed electromagnetic beam to be incident on a sample. The method further includes creating a spatially dependent relative phase difference between the electric field components of the beam. The beam is then polarized and the intensity is sampled at a plurality of locations with the multi-element detector. The method further includes synchronizing the detection of the intensity of the polarized pulsed electromagnetic beam with turning on and off the electromagnetic beam. The method may further comprise turning on and off the electromagnetic beam to produce a plurality of pulsed electromagnetic beams. In one aspect of the invention, the method includes expanding the beam. The method can be used in a monochromatic or spectroscopic mode. In a spectroscopic mode, the method further includes filtering the wavelengths of the beam spatially in a direction orthogonal to the direction of producing the spatially dependent phase difference, wherein the intensity of the polarized light beam is determined as a function of the spatially dependent relative phase shift in one direction and the wavelengths in another direction on a two-dimensional detector.

In yet another aspect of the present invention, an interferometer includes an electromagnetic source that turns on and off to produce a pulsed electromagnetic beam, a spatially dependent polarizing element and a multi-element detector. The interferometer may also include a beam expander that spatially expands the electromagnetic beam. The interferometer may also include a synchronizer coupled to the electromagnetic source and the multi-element detector, wherein the synchronizer causes the multi-element detector to measure the intensity of the pulsed electromagnetic beam as a function of position when the electromagnetic source is turned off. The interferometer may further include a wavelength-dispersing component that separates the component wavelengths of the electromagnetic beam.

DETAILED DESCRIPTION

Figure 3:
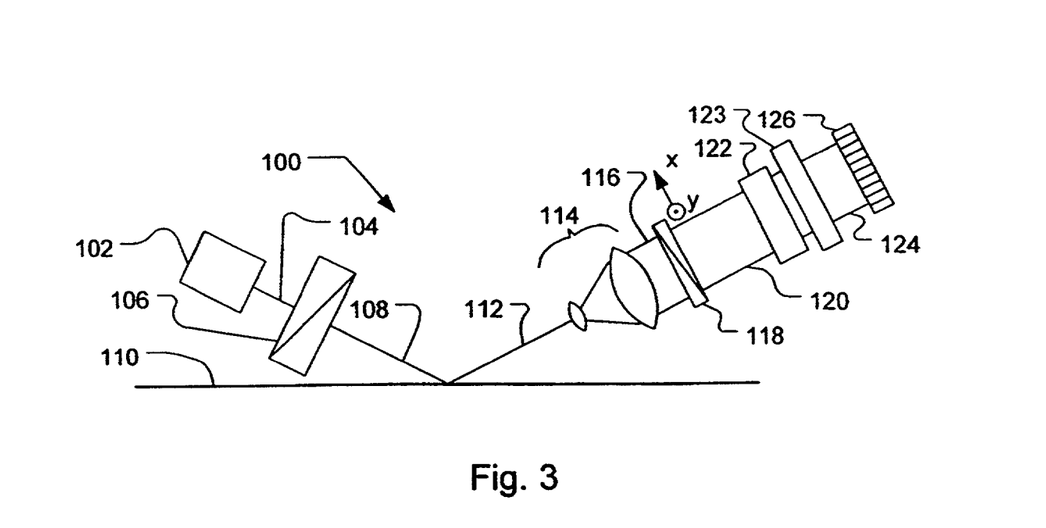
FIG. 3 is a block diagram of an ellipsometer with no moving parts and no time dependent phase modulator in accordance with an embodiment of the present invention.

In accordance with an embodiment of the present invention, a metrology device, such as an ellipsometer, is time independent so that it can be used with a pulsed light source, such as a flash bulb or pulsed laser. For example, FIG. 3 shows a block diagram of an ellipsometer 100 in accordance with an embodiment of the present invention. After the light beam is reflected from the sample 110, the beam is expanded and passed through a variable retarder 118 to introduce a spatially dependent phase shift. The expanded beam then passes through polarizer 122 and the intensity is measured using multi-element detector 126. Ellipsometer 100 may be used advantageously for semiconductor thin film applications. Due to its small size, it may be integrated into various semiconductor or other processor tools.

As shown in FIG. 3, ellipsometer 100 includes an electromagnetic source 102 that generates a collimated beam 104 of monochromatic or broadband radiation that is transmitted through polarizer 106 to produce a polarized beam 108. The polarized beam 108 is incident on and interacts with the sample surface 110 to produce a reflected beam 112. Reflected beam 112 has a modified polarization state compared to polarized beam 108. It should be understood that if desired, ellipsometer 100 may operate in transmission mode in which case the beam passes through the sample. For the sake of simplicity, the present disclosure will describe an ellipsometer operating in reflection mode, with the understanding that a transmitted beam may alternatively be used.

After reflection from the sample surface 110, the reflected beam 112 is expanded in the plane of the drawing (the x direction) by expander 114 to produce an expanded beam 116. It should be understood, however, that beam expander 114 is used to shape the beam so that it adequately fills the variable retarder 118 and a multi-element detector 126 with the reflected signal. If the reflected beam itself adequately fills the variable retarder 118 and multi-element detector 126, e.g., if electromagnetic source 102 produces the properly shaped beam, beam expander 114 is unnecessary.

The expanded beam 116 is then transmitted through a variable retarder 118 whose geometry is matched to the shape of the expanded beam. The variable retarder 118 has the property of creating a relative phase difference 6 between the electric field components parallel (ordinary or o) and perpendicular (extraordinary or e) to the optical axis of the variable retarder 118 in the x direction. The resulting phase shifted beam 120 is then transmitted through a polarizer (linear polarizer) 122. A multi-element detector 126 then records the intensity of resulting beam 124. The detector geometry is chosen to match the geometry of the beam expander 114 and variable retarder 118. The multi-element detector 126 may be a photodiode array (PDA), a multi-element charge coupled device (CCD), an avalanche photodiode array (APD), a multi-element photomultiplier, or even a multi-element charge injection device (CID) or some similar device. The choice of the appropriate multi-element detector depends on many variables, such as the available light throughput, needed measurement time, and of course, cost.

It should be understood that if desired, the expander 114 and variable retarder 118 may be located in the PSG, i.e., before the sample surface 110. In this embodiment, for example, the expanded beam is focused onto the sample surface 110.

In a spectroscopic embodiment, broadband radiation is emitted from source 102. Additionally, the light beam must be expanded in the y direction, which will be described below. An additional optical component, such as a band-pass filter array 123, is required to separate the various wavelengths of the beam. An appropriate band-pass filter 123 has a linear variation of the transmitted wavelength in the y direction. Band-pass filter 123 can also be made up of individual interferometric elements. Interferometric filters are composed of stacks of thin films with different thicknesses chosen such that essentially only one narrow, well-defined wavelength range is transmitted through the filter. It is possible to construct an interferometric filter employing a gradient in thickness of the thin films in one direction such that a continuous spectrum of wavelength filters is obtained. These kind of filters may be custom-manufactured by, e.g., Barr Associates, Inc. located in Westford, Mass. With the gradient oriented in the y direction and a multi-element detector 126 that has elements in the x and y directions, the detector 126 maps the intensity of the resulting beam as a function of retardance δ in the x direction and as a function of wavelength λ in the y direction. The intensities recorded by the detector 126 can then be analyzed to obtain the ellipsometry angles ψ and Δ as a function of wavelength.

The relative position of band-pass filter 123 may vary after beam 112 is adequately expanded, i.e., band-pass filter 123 may also be located immediately after beam 112 is expanded and before variable retarder 118, or even between variable retarder 118 and polarizer 122.

Figure 4:
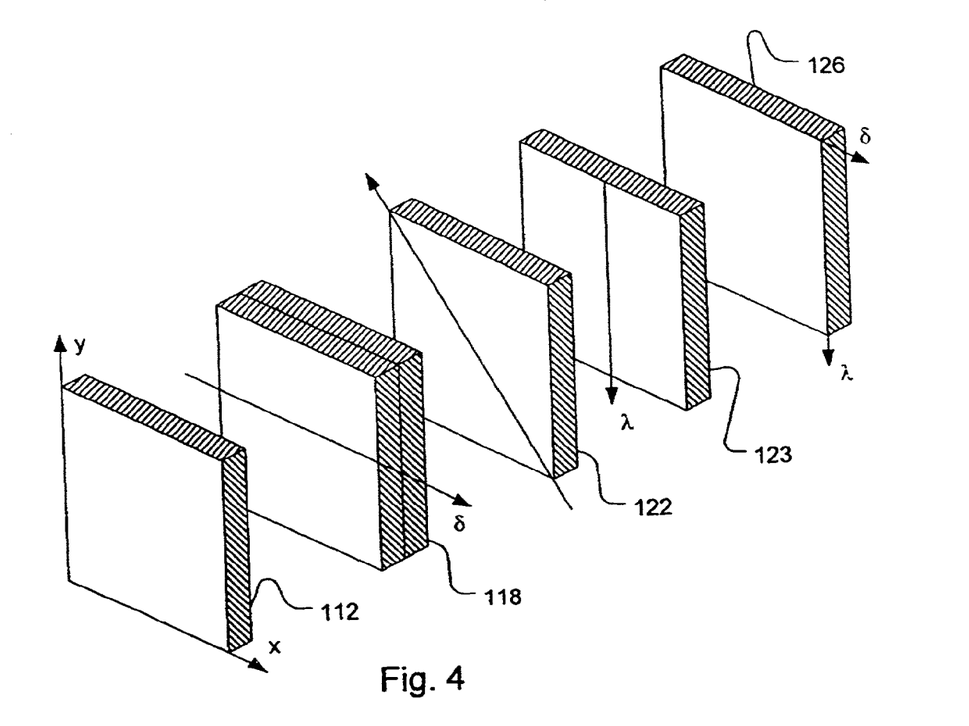
FIG. 4 shows a perspective view of the PSD from the ellipsometer in FIG. 3 when used in spectroscopic mode.

FIG. 4 shows a perspective view of the PSD after beam expansion in ellipsometer 100 in FIG. 3 where the expanded beam 112 is illustrated as plate 112 for the sake of simplicity. As shown in FIG. 4, spatial variable retarder 118 varies the phase δ along the x-axis and interferometric filter 123 varies the wavelength λ along the y-axis. The polarizer 122 creates the sinusoidal modulation of the intensity. Thus, as illustrated in FIG. 4, the detector 126 measures the intensity of the light beam as a function of phase δ along the x-axis and wavelength λ along the y-axis.

Figure 5:
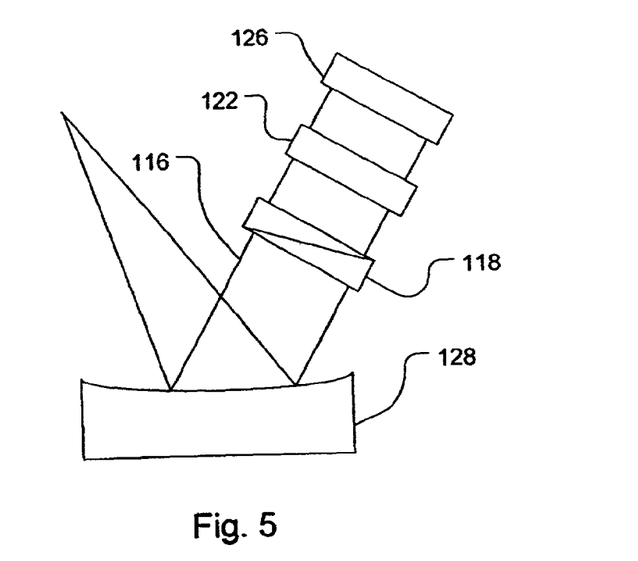
FIG. 5 shows a reflecting diffraction grating that expands and collimates the beam in the PSD.

Other hardware configurations can be devised for spectroscopic ellipsometry in accordance with the present invention, as described in U.S. application Ser. No. 09/929,625. For example, as shown in FIG. 5, a reflecting diffraction grating 128 is used to collimate the beam in reflection in the x direction as well as separate the wavelengths in the signal by diffraction in the y direction. In this case, the reflecting diffraction grating 128 replaces the interferometric filter 123 shown in FIGS. 3 and 4 and the collimating components of the beam expanding optics 114 shown in FIG. 3. In this configuration, the reflecting diffraction grating 128 operates as part of the expander in the ellipsometer used to expand the reflected beam to fill the variable retarder 118. Transmission gratings can also be employed to spread the beam in the y direction. See, for example, U.S. Pat. No. 5,392,116, issued Feb. 21, 1995, which is incorporated herein by reference.

Figure 6A:
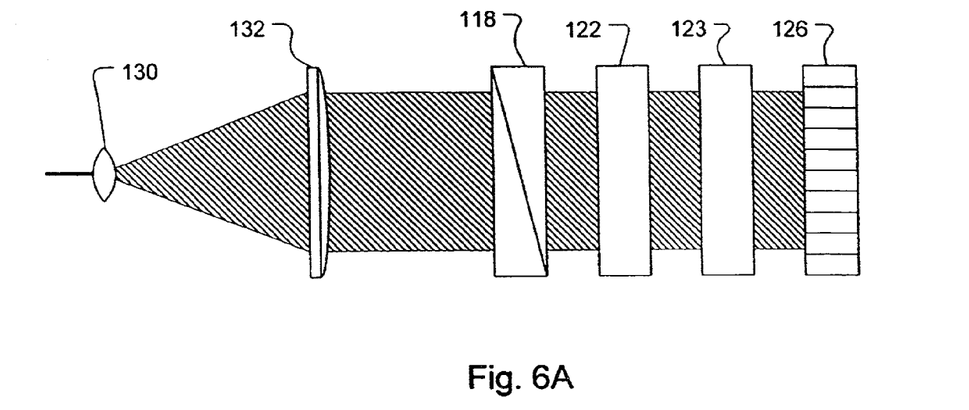
FIG. 6A shows a lens system to expand and collimate the beam to cover the entire PSD detector area.
Figure 6B:
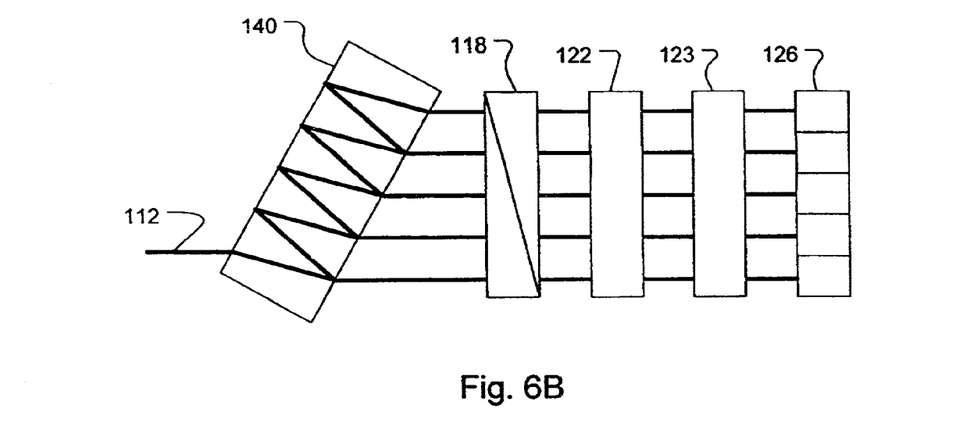
FIG. 6B shows an etalon that is used to spatially expand the reflected beam into several discrete beams to cover the entire PSD detector area.
Figure 6C:
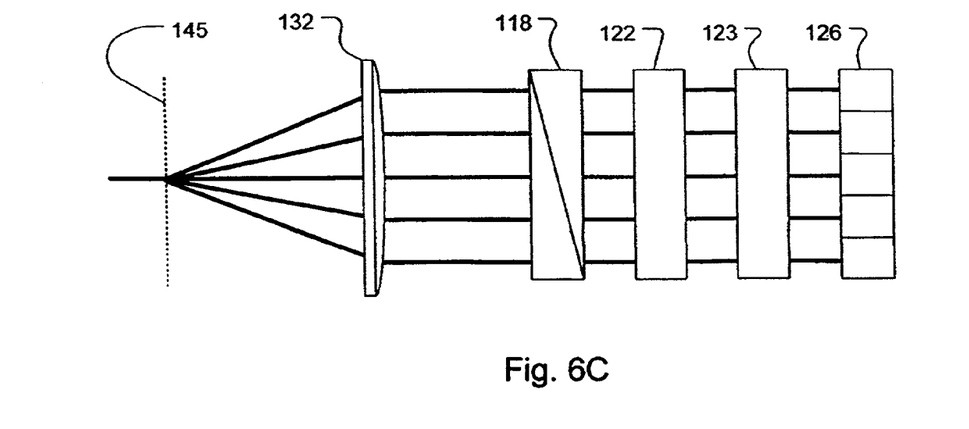
FIG. 6C shows transmission diffraction grating that is used to spatially expand the reflected beam to cover the entire PSD area.

Numerous techniques can be devised to expand the reflected beam 112 to fill the variable retarder 118 and detector 126. For example, as shown in FIG. 3 and in FIG. 6A, lenses 130 and 132 can be used to expand and collimate the reflected beam 112 to cover the desired PSD area. Alternatively, as shown in FIG. 6B, an etalon 140 can be used to divide the reflected beam 112 into a plurality of discrete beams to functionally spatially expand the beam. Multiple reflections inside the etalon 140 generate parallel beams of equal intensity from a properly coated etalon. The detector elements in detector 126 should then be aligned to the discrete beams produced by the etalon 140. Diffractive optics such as a grating 145 can also be used, along with collimating lens 132, to spatially expand the beam into a plurality of individual beams of equal intensity, as shown in FIG. 6C.

Figure 7A:
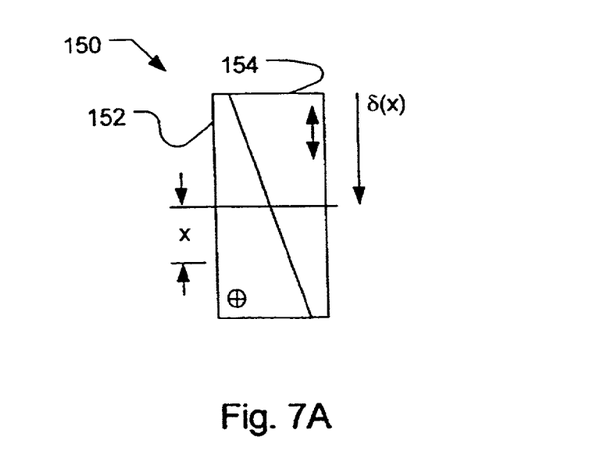
FIGS. 7A, 7B, and 7C show three embodiments of a variable retarder that may be used in the PSD shown in FIG. 3
Figure 7B:
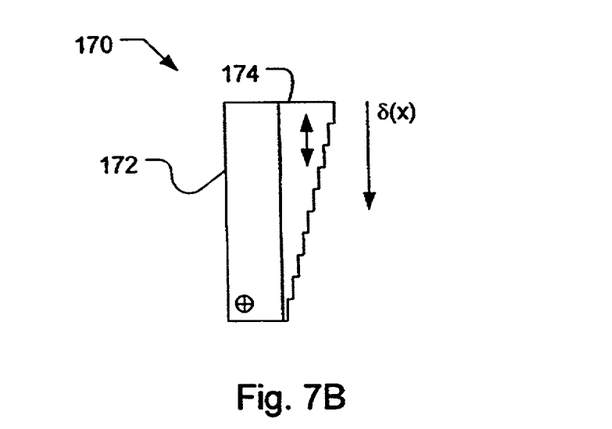
Figure 7C:
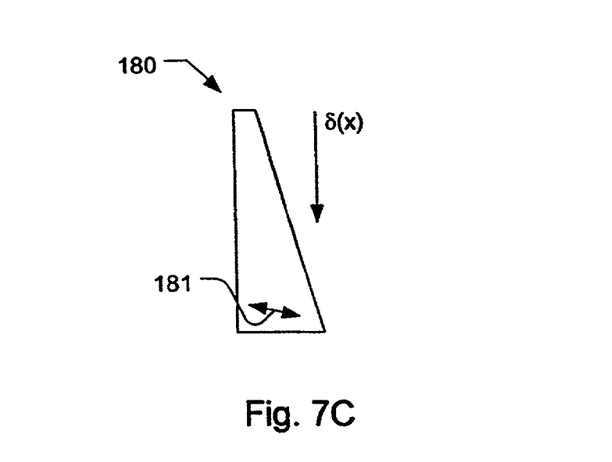

As described in U.S. application Ser. No. 09/929,625, many spatially variable retarders may be designed for use in the present invention. For example, FIGS. 7A, 7B, and 7C show three illustrative variable retarders that may be used with the present invention. The variable retarder 150 shown in FIG. 7A consists of two wedged plates 152 and 154 composed of birefringent material whose outer surfaces are orthogonal to the beam propagation direction. The optical axes of the plates 152 and 154 are perpendicular to each other. An example of variable retarder 150 is manufactured by InRad Inc. located at New Jersey. The effective retardance for variable retarder 150 assuming an orthogonal incident beam is given by:

$$\delta(x) = \frac{4\pi}{\lambda} \Delta n x \tan\Phi, \qquad \text{eq. 1}$$

where x is the distance from the center of the variable retarder 150, Δn is the birefringence (which is a function of wavelength λ), i.e., the difference between the ordinary and extraordinary refractive indexes assuming both wedges are made of the same material, and Φ is the wedge angle of the internal faces of the two birefringent plates 152 and 154. The angle Φ is preferably chosen so that the retardance 8 varies over a range of at least 2π radians for the wavelengths of interest. An additional complexity is that the o and e beams start to diverge at the interface of the two wedges and continue to diverge at the exiting air interface. Therefore, Φ should be chosen as small as possible to minimize the separation between the two polarization components. As shown in FIG. 3, it is desirable to locate the detector 126 as close as possible to the variable retarder 118. Alternatively, a lens following the variable retarder 118 may be used to correct this divergence.

FIG. 7B shows another example of a variable retarder 170 composed of two plates. The first plate 172 has two parallel faces. The second plate 174 has one flat face and a second face with a series of steps of different thicknesses. If desired, the second plate 174 may have a continuously changing thickness rather than a series of steps. The optical axes of the first plate 172 and the second plate 174 are perpendicular to each other similar to the variable retarder 150 described in FIG. 7A. The relative phase difference δ is once again a function of position from the center of the plate. The steps in plate 174 could also be varied in thickness in the y direction for spectroscopic applications to maintain a constant phase delay for each wavelength. This configuration of a variable retarder does not result in a divergence of the two o and e components of the polarized beam. The variable retarder shown in FIG. 7B is also useful in an interferometer.

FIG. 7C is another example of a variable retarder 180 composed of a single wedge. Variable retarder 180 is a made up of a single plate of birefringent material with non-parallel faces. The optical axis must be at a very small angle (almost parallel) to the beam propagation direction as indicated by arrow 181. Thus, the optical axis is at an oblique angle with the direction of propagation of the electromagnetic beam. This geometry creates an effective birefringence given by the projection of the ordinary and extraordinary indices of refraction to the plane perpendicular to the direction of propagation.

It should be understood that other variable retarders could be used. For example, a liquid crystal array, where it is possible to control the birefringence of individual pixels in the x and y directions may be used, as described in T. Horn and A. Hofmann, "Liquid Crystal Imaging Stokes Polarimeter", ASP Conference Series Vol. 184, pp. 33–37 (1999), which is incorporated herein by reference. A depolarizer, such as the one fabricated by Karl Lambrecth Co., located in New Jersey, may also be used as a variable retarder. Moreover, a variable retarder that uses artificial dielectrics may be used, such as that described in D. R. S. Cumming and R. J. Blaikie, "A Variable Polarization Compensator Using Artificial Dielectrics", Opt. Commun. 163, pp. 164–168 (1999), which is incorporated herein by reference.

Figure 8:
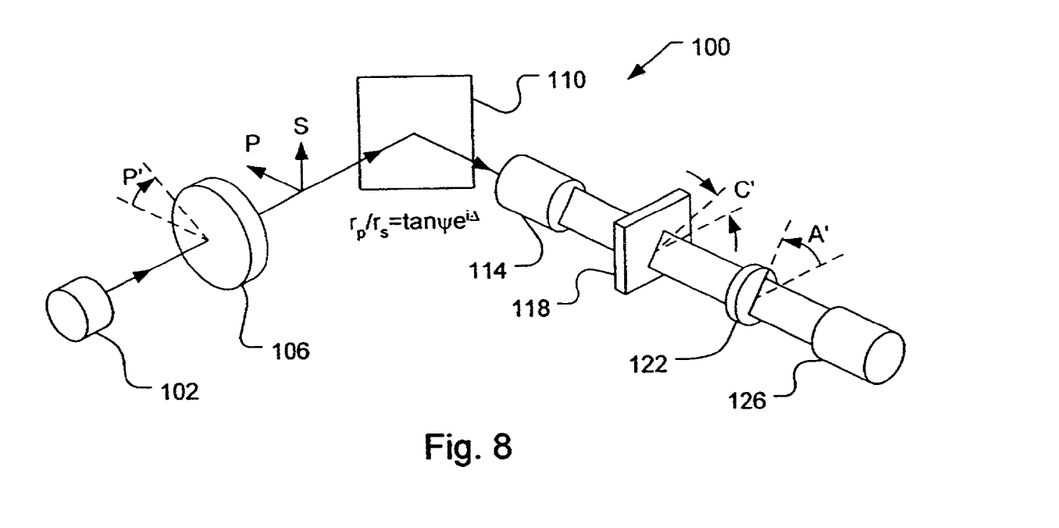
FIG. 8 shows a perspective view of an ellipsometer with no moving parts indicating the calibration parameters.

For the system shown in FIG. 3, the Mueller formalism can be used to yield the following dependence for the intensity as measured by the multi-element detector 126 as a function of δ(x):

$$I = I_0\{1 + \sin 2(C'-A') \sin 2(C'-Q) \cos \delta(x) \cos 2\chi + \cos 2(C'-A')\cos 2(C'-Q)\cos 2\chi - \sin 2(C'-A')\sin\delta(x)\sin 2\chi\} \quad \text{eq. 2}$$

where $I_0$ is the intensity without polarization, C' is the angle of the optical axis of the variable retarder 118, and A' is the angle of the transmission axis of the polarizer 122. Both the C' and A' angles are measured with respect to the plane of incidence, as shown in FIG. 8, which shows a perspective view of ellipsometer 100. The retardance of the variable retarder 118 is represented in equation 2 by δ(x). The ellipticity angle is represented by χ and the tilt angle defining the polarization state of the reflected beam is represented by Q.

Figure 9:
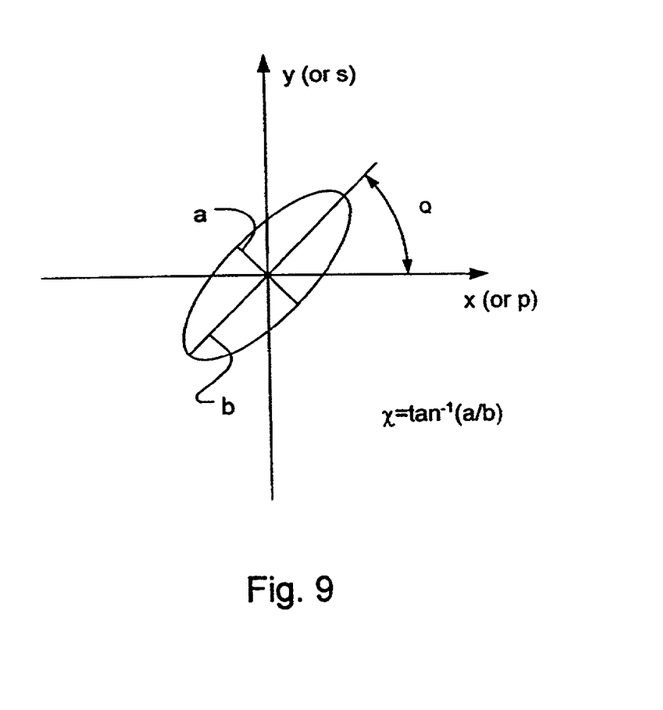
FIG. 9 shows a representation of the polarization state of an electromagnetic beam in terms of its ellipsometric angles x and Q.

FIG. 9 is a representation of a polarization state of an electromagnetic beam in terms of its ellipsometry angles χ and Q, with the x-axis parallel to the plane of incidence. When Q is greater than zero, the angle is defined as counter-clockwise for an incoming beam, as shown in FIG. 9. The sign of χ determines the handedness of the polarization state, i.e., positive χ indicates left-handed rotation, whereas negative χ indicates right-handed rotation, also shown in FIG. 9.

The quantities χ and Q are related to the ellipsometry angles χ i and Δ by:

$$\cos 2\psi = \frac{\cos 2P' - \cos 2Q \cos 2\chi}{1 - \cos 2Q \cos 2\chi \cos 2P'} \quad \text{eq. 3A}$$

$$\tan\Delta = -\frac{\tan 2\chi}{\sin 2Q} \quad \text{eq. 3B}$$

where P' is the angle of the transmission axis of the polarizer 106 with respect to the plane of incidence, as shown in FIG. 8. Ellipsometry angles and equations 3A and 3B are described in more detail in Joungchel Lee, P. I. Rovira, Ilsin An, and R. W. Collins, "Rotating-Compensator Multichannel Ellipsometry: Applications for Real Time Stokes Vector Spectroscopy of Thin Film Growth", Rev. Sci. Intrum. 69, pp. 1800–1810 (1998), which is incorporated herein by reference. The ellipsometry angles ψ and Δ can then be modeled using, e.g., the Fresnel formalism to obtain the thin film properties of the sample.

In order to obtain χ and Q, the intensity given by equation 2 may be analyzed, e.g., using regression analysis, once the intensities of the multi-element detector 126 are measured. An additional approach shows the normalized intensity written as:

$$I' = 1 + \alpha \cos \delta + \beta \sin \delta \quad \text{eq. 4}$$

Where α and β are described by the following equations:

$$\alpha = \frac{\sin 2(C' - A')\sin 2(C' - Q)\cos 2\chi}{1 + \cos 2(C' - A')\cos 2(C' - Q)\cos 2\chi} \quad \text{eq. 5A}$$

$$\beta = \frac{-\sin 2(C' - A')\sin 2\chi}{1 + \cos 2(C' - A')\cos 2(C' - Q)\cos 2\chi}. \quad \text{eq. 5B}$$

One advantageous configuration of angles is P'=45°, C'=0°, and A'=−45°, but other configurations may be used.

Figure 10A:
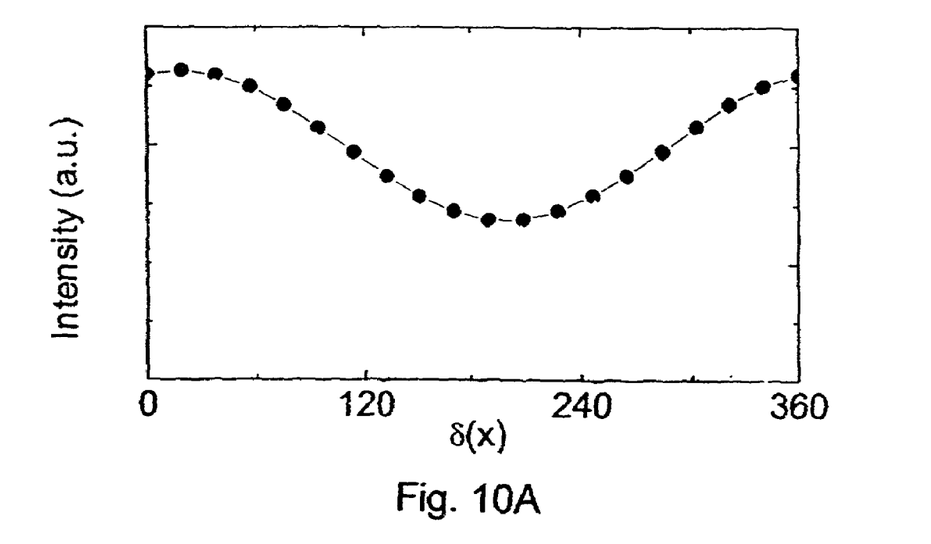
FIG. 10A shows the modulated intensity signal detected by the multi-element detector.

FIG. 10A shows the modulated intensity signal in arbitrary units detected by the multi-element detector 126. If the intensity is modulated by 2π radians and the photodetector array contains N detectors, as shown in FIG. 10A, the Fourier coefficients can be obtained from the following relations:

$$\alpha = \frac{1}{I_{sum}} \sum_{q=1}^{N} I_{\exp,q} \cos\delta_q, \quad \text{eq. 6A}$$

$$\beta = \frac{1}{I_{sum}} \sum_{q=1}^{N} I_{\exp,q} \sin\delta_q, \quad \text{eq. 6B}$$

$$I_{sum} = \sum_{q=1}^{N} I_{\exp,q}. \quad \text{eq. 6C}$$

Figure 10B:
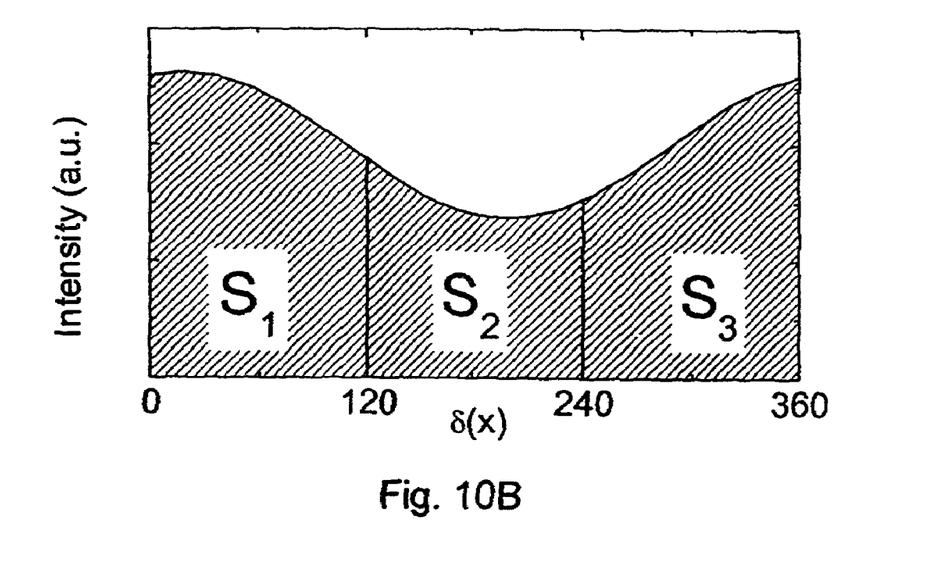
FIG. 10B shows the same modulated intensity detected by three detectors, which collect the partial integrals of the modulated intensity.

In an alternative approach, using a multi-element detector with a limited number of elements, the output of each element is proportional to the area of the intensity curve, as shown in FIG. 10B for the case of a three-element detector. This technique has the potential to improve the data collection throughput. In FIG. 10B, each element covers one third of the total modulation. Each detector will collect an intensity that is proportional to the partial integrals of I(x). The integrals of the intensity $S_j$ (j=1,2,3, . . . ) are referred to in the literature as Hadamard sums. Therefore, for the case of three detectors and a complete modulation period, the following can be written:

$$S_m = \int_{2\pi(m-1)/3}^{2\pi m/3} I_0[1 + \alpha\cos(\delta(x)) + \alpha\cos(\delta(x))] d\delta(x), \quad \text{eq. 7}$$

where: m=1,2,3.

Thus:

$$S_1 = I_0\left(\frac{2}{3}\pi + \frac{\sqrt{3}}{2}\alpha + \frac{3}{2}\beta\right), \quad \text{eq. 8A}$$

$$S_2 = I_0\left(\frac{2}{3}\pi - \sqrt{3}\,\alpha\right), \quad \text{eq. 8B}$$

$$S_3 = I_0\left(\frac{2}{3}\pi + \frac{\sqrt{3}}{2}\alpha - \frac{3}{2}\beta\right). \quad \text{eq. 8C}$$

Inverting these equations, the normalized Fourier coefficients will be given by:

$$\alpha = \frac{2\pi}{3\sqrt{3}} \frac{(-S_1 + 2S_2 - S_3)}{(S_1 + S_2 + S_3)}, \quad \text{eq. 9A}$$

$$\beta = \frac{2\pi}{3} \frac{(S_1 - S_3)}{(S_1 + S_2 + S_3)}. \quad \text{eq. 9B}$$

Summarizing, in order to obtain the ellipsometry angles ψ and Δ associated with a thin film stack on a sample, the intensity as a function of detector position is first measured. The quantities α and β are calculated either from equations 6A–6C, or equations 9A–9B. Next, the angles χ and Q are calculated from equations 5A–5B after inversion. Finally, the ellipsometry angles ψ and Δ are obtained from equations 3A–3B.

In addition, it should be understood that PSD shown in FIG. 4 may be used with metrology instruments other than the ellipsometer shown in FIG. 3. For example, if desired, the PSD with or without a beam expander may be used in an interferometer 300, shown in FIG. 11. Interferometer 300 includes an electromagnetic source 302 followed by a half-wave plate 303 and a polarizer 304. A beam splitter 305 directs the electromagnetic beam towards the sample 310. A Wollaston prism 306 splits the light beam into two light beams, which are focused on the sample by lens 308. The two beams are reflected off sample 310 and travel back through lens 308 and prism 306, where the two beams are recombined into a single superimposed beam before passing through beam splitter 305. The beam is then expanded by beam expander 312 and passes through a spatial variable retarder 314. If the beam does not need expanding, as discussed above, beam expander 312 need not be used. The beam passes through a polarizer 316 and an interferometric filter 318 (if desired) prior to being received by multi-element detector 320. Thus, the multi-element detector 320 receives a single superimposed electromagnetic beam. The single beam received by detector 320 is appropriately shaped to fill the detector 320 by beam expander 312 (if beam expansion is necessary) or by other optical elements, e.g., lens 308, prism 306, beam splitter 305, or the light source 302 itself, (if beam expansion is not used). In addition, if desired, spatial variable retarder 314 may be a single plate of birefringent material with non-parallel faces, with the optical axis at a small angle (almost parallel) to the beam propagation direction, as discussed in FIG. 7C.

Figure 12:
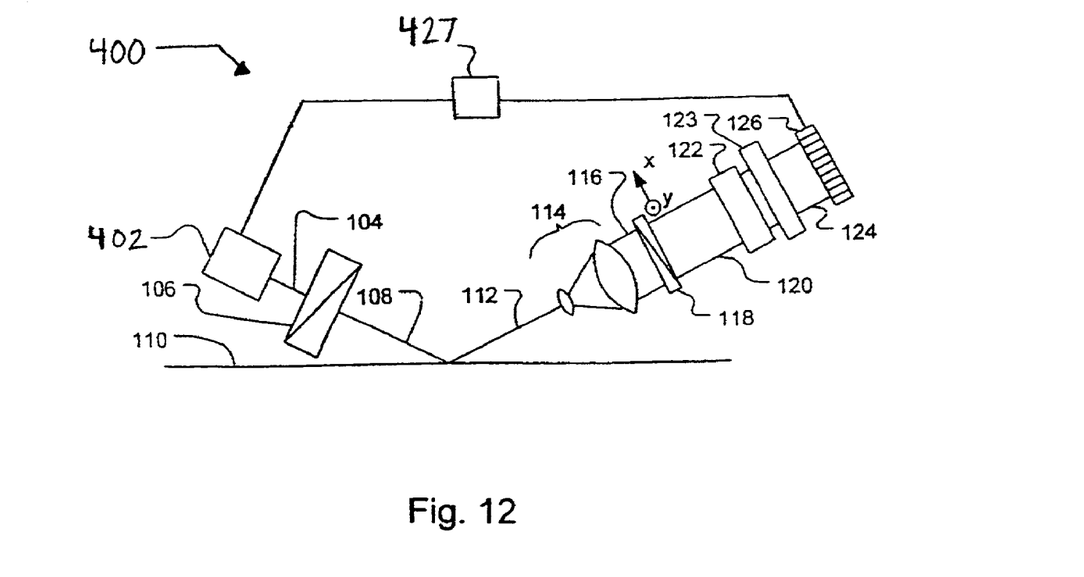
FIG. 12 shows the ellipsometer of FIG. 3 in accordance with an embodiment of the present invention.

In accordance with other embodiments of the present invention, FIG. 12 shows ellipsometer 400, which is similar to ellipsometer 100 shown in FIG. 3, except ellipsometer 400 uses a pulsed light source 402. Pulsed light source 402 may be, for example, a Xenon flash bulb, such as that manufactured by PerkinElmer, located in Santa Clara, Calif. Such flash bulb is a Xenon arc lamp, with a typical wavelength range from 160 nm to 4 μm, stability of better than 3%, and intensity flux up to 120 μJ/cm². This lamp can be pulsed at frequencies as high as 530 Hz, depending upon the choice of electronics. The decay time of the intensity of one pulse can be as long as 150 μs, again, depending upon the choice of electronics.

For a monochromatic system, a pulsed laser may be used as pulsed light source 402, such as that manufactured by Melles Griot, located Carlsbad, Calif. Laser source parameters vary depending on the desired wavelength and intensity. Furthermore, multiple pulsed discrete laser lines may be used in a pseudo-spectroscopic arrangement. Alternatively, a single pulsed laser, e.g., a NdYAG laser, that includes the fundamentals and overtones may be used to create a pseudo-spectroscopic arrangement.

The use of a pulsed light source offers many advantages over conventional continuous light sources. A pulsed light source enables energization of the light source to be confined to the time over which a measurement is to be made. This reduces the time over which the sample is illuminated, thereby reducing possible negative effects on the sample that may occur when it is illuminated with a focused, highly radiant light beam. Also, power consumption is reduced and the life of the light source is significantly extended. Furthermore, unlike a conventional detector readout used in conjunction with a continuous light source, no mechanical shutter is needed to block the electromagnetic beam if a background measurement is needed because the pulsed light source is dark between pulses.

However, conventional metrology devices cannot utilize a pulsed light source such as a flash bulb or a pulsed laser, as conventional metrology devices are time dependent, causing synchronization problems, and thus, accuracy problems when used with a pulsed light source. The use of a pulsed light source is possible according to the present invention because ellipsometer 400 of FIG. 12 has no moving parts, e.g., no time dependent phase modulators, as the spatially dependent polarizing element consisting of variable retarder 118 and linear polarizer 122 in FIG. 12 produces a spatially dependent polarization state. Another advantage of ellipsometer 400 is that it can simultaneously collect a matrix of phase shift range and spectral wavelength range. It is hence insensitive to intensity fluctuations in the illuminating beam and in pulse-to-pulse intensity variations. It should also be understood that interferometer 300 of FIG. 111 may similarly use a pulsed light source in place of light source 302.

As shown in FIG. 12, ellipsometer 400 may also include synchronizer 427 coupled to pulsed light source 402 and multi-element detector 126. Synchronizer 427 causes multi-element detector 126 to measure the intensity of the electromagnetic beam as a function of position after pulsed light source 402 emits a short pulse of light, e.g., for 150 μs. Consequently, multi-element detector 126 is synchronized with pulsed light source 402 such that multi-element detector 126 is reading out the accumulated charge only when pulsed light source 402 is off, i.e., when no light is produced.

Figure 11:
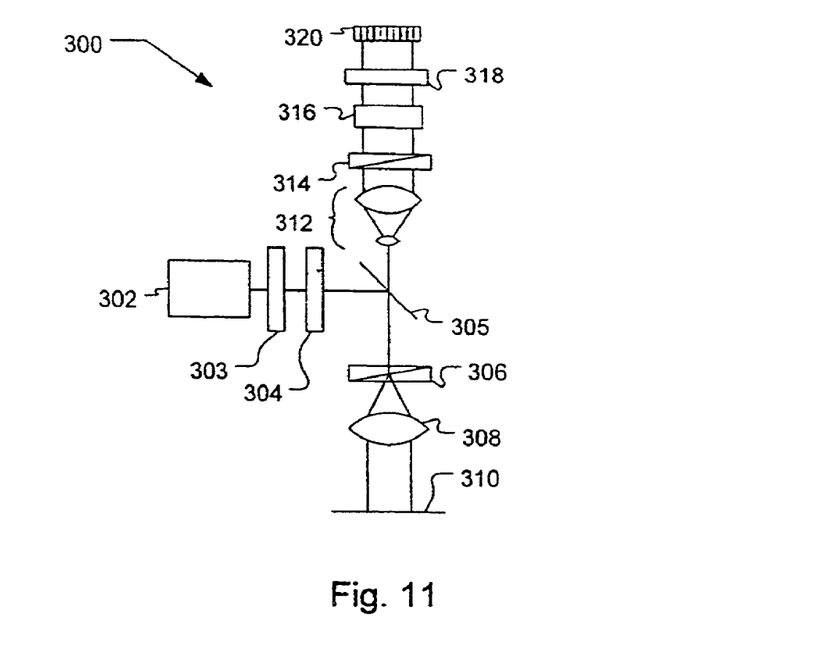
FIG. 11 is a block diagram of an interferometer in accordance with an embodiment of the present invention.

It should also be understood that interferometer 300 of FIG. 11 may similarly include a synchronizer coupled to a pulsed light source and the multi-element detector, causing the multi-element detector to detect the intensity of the electromagnetic beam when the pulsed light source is off.

Synchronizer 427 may operate in several ways. For example, synchronizer 427 may receive a signal from multi-element detector 126 indicating when multi-element detector 126 is beginning to measure the amount of light detected, i.e., read out the charge. Based on the signal from multi-element detector 126, synchronizer 427 can turn pulsed light source 402 on or off so that multi-element detector 126 is reading only when pulsed light source 402 is off and is not reading when pulsed light source 402 is on, i.e., producing light. In another example, synchronizer 427 may receive a signal from pulsed light source 402 indicating when pulsed light source 402 is on or off. Synchronizer 427 can then cause multi-element detector 126 to measure the accumulated charge during the appropriate period, i.e., when pulsed light source 402 is off. In yet another example, an independent frequency source may turn multi-element detector 126 and pulsed light source 402 on and off in a complimentary fashion so that multi-element detector 126 reads out the accumulated charge when pulsed light source 402 is off. There are also many other ways in which synchronizer 427 can work that are well within the understanding of a person of ordinary skill in the art.

In one embodiment, synchronizer 427 permits a user to specify the number of pulses of light during data collection, thereby averaging the signal over several light pulses. Thus, data may be read after a plurality of pulses, e.g., after every ten pulses of light or after every fifty pulses of light, when pulsed light source 402 is on.

Figure 13A:
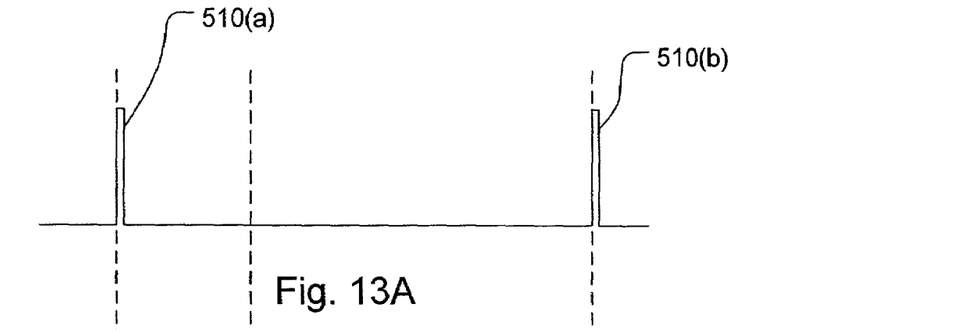
FIGS. 13A, 13B, 13C and 13D show the synchronization of a CCD reading and a pulsed light source in accordance with an embodiment of the present invention.

FIGS. 13A, 13B, 13C, and 13D show the schematics of the time synchronization of a multi-element detector 126 reading and a pulsed light source 402. In FIG. 13A, the first signal indicates the Start pulse 510(a), which occurs at time t0. Another Start pulse 510(b) occurs at time t3. Start pulses 510(a) and 510(b) also define the Stop pulse for the previous scans. The time between two consecutive Start pulses 510(a) and 510(b) is the total cycle time.

Figure 13B:
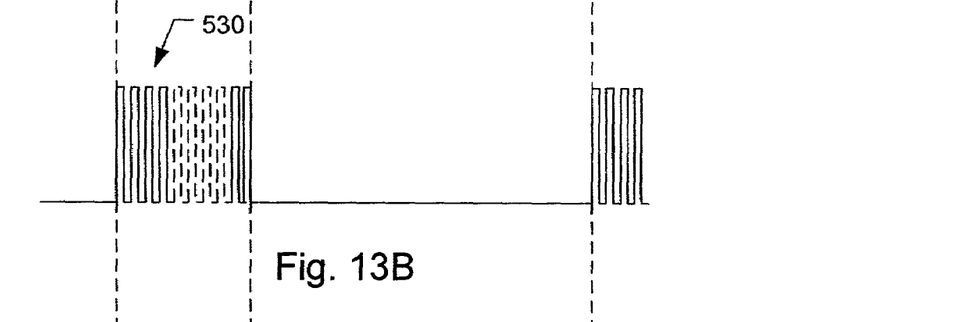

After Start pulse 510(a), the multi-element detector 126, which may be a CCD, begins reading out the accumulated charge from each element from a previous scan as indicated by the number of pulses 530 in FIG. 13B. The total time for reading all the elements depends on the internal clock of the electronics, the number of elements and the mode of operation. Typically, there a large number of elements, and thus a correspondingly large number of pulses are required, indicated by the pulses 530 with broken lines. At time t1 the multi-element detector 126 is finished reading out the accumulated charge.

Figure 13C:
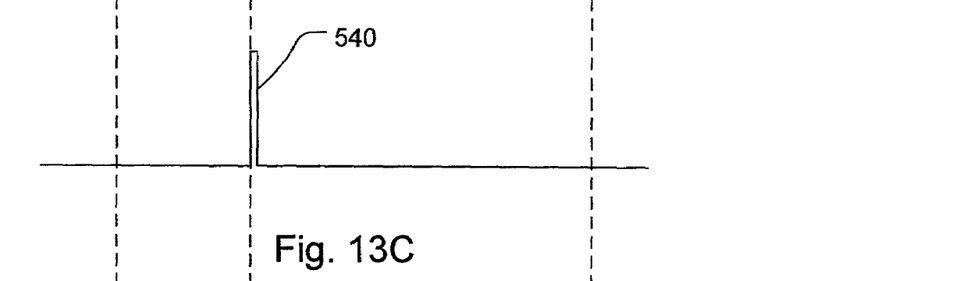
Figure 13D:
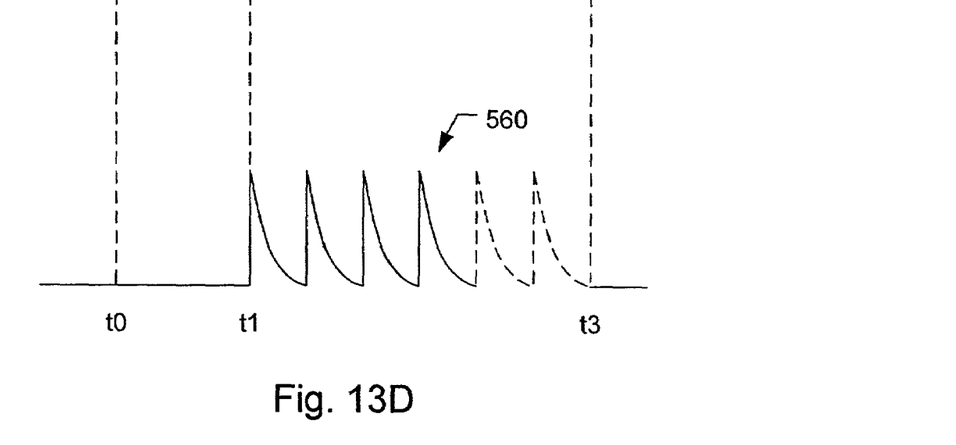

As shown in FIG. 13C, after reading out all the data, the multi-element detector 126 produces an End of Scan (EOS) pulse 540 at time t1, that can be used for synchronization of external equipment, such as the pulsed light source 402. After EOS pulse 540 is produced, the pulsed light source 402 produces one or more light pulses depending on how much energy is needed, as shown in pulse train 560 of FIG. 13D. As the intensity of the flash lamp has an exponential temporal decay, the integration time of the multi-element detector 126 must be a function of the number of flash pulses, so that it is guaranteed that a complete train of pulses fits into the cycle ending at time t3.

Thus, as can be seen in FIGS. 13A, 13B, 13C, and 13D, multi-element detector 126 reads out data, i.e., accumulated charge, while the pulsed light source 402 is off, i.e., not producing light pulses, and while the pulsed light source 402 is on, i.e., producing light pulses, multi-element detector 126 is off, i.e., not reading out data.

In another embodiment, the pulsed light source 402 remains on, i.e., the light source 402 continuously produces pulses of light even while multi-element detector 126 is reading out the accumulated charge. However, difficulties arise from such an embodiment. For example, because the accumulated charge in a multi-element detector 126 is typically read out in a serial fashion, i.e., element by element (or in some cases, row by row), if continuously pulsed light is used, the last element in the multi-element detector 402 will be exposed to pulses of light after a previous, i.e., the first, element has been read out. By using multiple cycles, i.e., exposing and reading out, it may be possible to average the accumulated charge over multiple cycles thereby compensating for the difference in the accumulated charge from one element to the next in any one cycle.

Although the present invention is illustrated in connection with specific embodiments for instructional purposes, the present invention is not limited thereto. Various adaptations and modifications may be made without departing from the scope of the invention. For example, the ellipsometer in accordance with the present invention may operate in either reflection or transmission mode. Moreover, a single wavelength or multiple wavelengths may be used. Various expanders may be used to expand the reflected (or transmitted) beam to cover the variable retarder. Additionally, various variable retarders may be used in accordance with the present invention. Therefore, the spirit and scope of the appended claims should not be limited to the foregoing description.

What is claimed is:

1. A metrology device that detects the polarization state of an electromagnetic beam that is incident on a sample, said device comprising:
    a polarization state generator, including an electromagnetic source that is a flash bulb that turns on and off to produce a pulsed electromagnetic beam with multiple wavelengths, wherein the polarization state generator produces a pulsed electromagnetic beam of known polarization state that is incident on the sample;
    a spatially dependent polarizing element in the path of the pulsed electromagnetic beam that varies the phase of the pulsed electromagnetic beam spatially along a first direction;
    a wavelength-dispersing component within the path of the pulsed electromagnetic beam, the wavelength-dispersing component separates the component wavelengths of the pulsed electromagnetic beam along a second direction; and
    a multi-element detector within the path of the pulsed electromagnetic beam after the spatially dependent polarizing element, wherein the multi-element detector detects the intensity of the pulsed electromagnetic beam as a function of phase along the first direction and as a function of wavelength along the second direction.

2. The metrology device of claim 1, wherein the spatially dependent polarizing element comprises:
a spatially variable phase retarder; and
a polarizer after the spatially variable phase retarder.

3. The metrology device of claim 1, further comprising a beam expander within the path of the pulsed electromagnetic beam before the spatially dependent polarizing element.

4. The metrology device of claim 3, wherein the beam expander and the spatial dependent polarizing element are located in the pulsed electromagnetic beam path after interaction with the sample.

5. The metrology device of claim 1, further comprising a synchronizer coupled to the electromagnetic source and the multi-element detector, wherein the synchronizer causes the multi-element detector to read out the intensity of the pulsed electromagnetic beam as a function of position when the electromagnetic source is turned off.

6. The metrology device of claim 5, wherein the electromagnetic source produces a plurality of pulsed electromagnetic beams after the synchronizer causes the multi-element detector to detect the intensity of the pulsed electromagnetic beam as a function of position.

7. A method of ellipsometrically measuring a sample, the method comprising:
turning on and off a broadband electromagnetic beam to produce a pulsed electromagnetic beam to be incident on a sample;
polarizing the pulsed electromagnetic beam prior to being incident on the sample;
producing a spatially dependent relative phase difference between the electric field components of the pulsed electromagnetic beam in a first direction;
polarizing the pulsed electromagnetic beam after a spatially dependent relative phase difference is produced;
filtering the wavelengths of the pulsed electromagnetic beam spatially in a second direction that is perpendicular to the first direction; and
detecting the intensity of the polarized pulsed electromagnetic beam at a plurality of positions as a function of the spatially dependent relative phase shift in the first direction and the wavelengths in the second direction.

8. The method of claim 7, further comprising turning on and off the electromagnetic beam to produce a plurality of pulsed electromagnetic beams.

9. The method of claim 7, further comprising expanding the pulsed electromagnetic beam prior to producing a spatially dependent relative phase difference.

10. The method of claim 7, further comprising:
reading out the detected intensity of the polarized pulsed electromagnetic beam at a plurality of positions; and
synchronizing the reading out the detected intensity of the polarized pulsed electromagnetic beam with the turning off of the electromagnetic beam.

11. An apparatus for measuring a characteristic of a sample, the apparatus comprising:
a flash bulb light source that can be turned on and off to produce a pulsed electromagnetic beam with multiple wavelengths;
a polarizer in the path of the pulsed electromagnetic beam, wherein the polarized pulsed electromagnetic beam is incident on the sample;
means for producing a spatially dependent phase shift in the pulsed electromagnetic beam, the means for producing a spatially dependent phase shift producing a phase shifted beam wherein the phase shift is spatially dependent along a first direction;
means for polarizing within the path of the phase shifted beam, the means for polarizing producing a polarized phase shifted beam;
means for dispersing the wavelengths of the expanded pulsed electromagnetic beam along a second direction, the means for dispersing the wavelengths being in the path of the expanded pulsed electromagnetic beam; and
means for measuring the intensity of the polarized phase shifted beam as a function of phase shift in the first direction and as a function of wavelengths in the second direction, the means for measuring being in the path of the polarized phase shifted beam.

12. The apparatus of claim 11, the apparatus further comprising a means for expanding the pulsed electromagnetic beam, the means for expanding being in the path of the pulsed electromagnetic beam.

13. The apparatus of claim 11, wherein the means for producing a spatially dependent phase shift in the pulsed electromagnetic beam comprises a spatial variable phase retarder.

14. The apparatus of claim 11, further comprising a means for synchronizing the means for measuring the intensity of the polarized phase shifted beam as a function of position with the turning on and off of the light source.

15. The apparatus of claim 14, wherein the means for synchronizing comprises a synchronizer coupled to the light source and to the means for measuring the intensity of the polarized phase shifted beam, wherein the synchronizer causes the means for measuring the intensity of the polarized phase shifted beam to read out data when the light source is turned off.

16. The apparatus of claim 15, wherein the light source produces a plurality of pulsed electromagnetic beams after the synchronizer causes the means for measuring the intensity of the polarized phase shifted beam to read out data.

* * * * *